United States Patent [19]

Grattoni et al.

[11] Patent Number: 4,627,096
[45] Date of Patent: Dec. 2, 1986

[54] PROCEDURE AND APPARATUS FOR THE SURVEY OF THE IMPRESSION MADE ON A SPECIMEN IN MEASURING THE HARDNESS AT PENETRATION

[75] Inventors: Paolo Grattoni, Collegno; Giulio Barbato, Turin, both of Italy

[73] Assignee: Consiglio Nazionale Delle Ricerche, Italy

[21] Appl. No.: 704,536

[22] Filed: Feb. 22, 1985

[30] Foreign Application Priority Data

Feb. 24, 1984 [IT] Italy .................. 67181 A/84

[51] Int. Cl.$^4$ .............................................. G06K 9/00
[52] U.S. Cl. .......................................... 382/8; 73/81; 358/107
[58] Field of Search ................... 73/81; 356/376, 378; 382/8; 358/107

[56] References Cited

U.S. PATENT DOCUMENTS

| | | | |
|---|---|---|---|
| 4,147,052 | 4/1979 | Tsujiuchi et al. | 356/378 |
| 4,255,966 | 3/1981 | Batie et al. | 73/81 |
| 4,275,966 | 6/1981 | Kleesattel | 73/81 |

FOREIGN PATENT DOCUMENTS 0149457  7/1985  European Pat. Off. .......... 382/19
0000738  1/1983  Japan ............................ 73/81

OTHER PUBLICATIONS

Abdou et al, "Quantitative Design and Evaluation of Enhancement/Thresholding Edge Detectors", *Proceedings of the IEEE*, vol. 67, No. 5, May 1979.

*Primary Examiner*—Leo H. Boudreau
*Assistant Examiner*—Jose Le Couso
*Attorney, Agent, or Firm*—McGlew and Tuttle

[57] ABSTRACT

The specimen (P) carrying the impression (I) is illuminated to create a variation of the impression luminance respect to the neighboring zone, and the image magnification of the impression is then performed by an optical system (OS). The magnified image is scanned with a telecamera (VC) to generate image electrical signals carrying informations indicative of the image luminance. By a technique of image segmentation, a computer (CS) draws from these image signals, position data of a group of image points taken, according to predetermined selection criteria, as belonging to the sides of the impression contour (I). Through the position data of at least some of such points, the position of characteristic points of the impression, for example the impression vertices in the Vickers hardness test, is then extrapolated or interpolated.

27 Claims, 5 Drawing Figures

PROCEDURE AND APPARATUS FOR THE SURVEY OF THE IMPRESSION MADE ON A SPECIMEN IN MEASURING THE HARDNESS AT PENETRATION

BACKGROUND OF THE INVENTION

1. Field of the Invention

The present invention refers to a procedure and an apparatus for the survey of the impression made on a specimen in measuring the hardness at penetration, and in particular, for the determination of the position of characteristic points of such impression, for example, the vertices of the Vickers impression or the ends of two orthogonal diameters of the Brinell impression.

The invention refers in particular to a procedure of the type in which the specimen is illuminated in such a way as to produce, in correspondence of the impression, a luminance variation respect to the surrounding zone, and in which the impression image is then magnified by an optical system.

2. Summary of the Prior Art

As everybody knows, the hardness at penetration is given, substantially, by the ratio between the applied load and the surface area of the impression produced on a specimen by a indentor. The indentor of the Vickers hardness test is a square-based pyramidal diamond; in the Brinell hardness test it is a ball made of steel or of tungsten carbide. According to the known technique, the characteristic measures (diagonals, diameters, etc.) of the impression are determined by means of a good microscope, with magnifications of 100–650 diameters, equipped with a micrometer eyepiece under the axis of which the specimen with the impression is brought.

The surface area of the impression is then calculated on the base of the means value of the characteristic measures thus obtained.

The hardness measurement so carried out results hardly repeatable and, what is more serious for practical purposes, is affected by a remarkable uncertainty; not only the hardness values measured on the same specimen by using different test machines may result different between them, but also measurements performed by two operators using the same test machine may result different even to a remarkable degree. The main limit, inherent in the method of measurement described above is due to the subjective error by the operator, in particular when measuring the lengths or the characteristic dimensions of the impression.

Further limits of the conventional method of hardness measurement at penetration stem from the laboriousness and long time required by the measurement itself. The stress resulting by long lasting observations performed when using hardometers equipped with microscopes (usually with a single eyepiece) tends to reduce the operator's concentration capacity and, therefore, to increase the inaccuracy and uncertainty of the measurement.

Methods and procedures have been proposed with a view of reducing the incidence of the subjective error by the operator, for example by taking the mean value of the measurements performed by two operators. Such methods, far from having removed the problem of the subjective factor in determining the hardness value, though allowing for a modest reduction of the measurement uncertainty, require long measurement times and thus much greater costs.

It has been found that the magnitude of discrepancies between measurements carried out by several operators is of the same order as the optical system resolution. As a consequence, it has been suggested to use optical instruments having a better resolution. However, investigations carried out to this purpose on images of impressions viewed through scanning electronic microscopes have shown that the impression edges are not well defined at all. It could be stated then, that the above mentioned subjective error committed by the operator might be probably due to a different and subjective way of locating the characteristic points of the impression which actually have a locally undefined configuration.

SUMMARY OF THE INVENTION

The object of this invention is to permit the almost complete elimination of the subjective evaluation factors in the hardness measurement at penetration and, moreover, to permit a rapid and reliable execution of the measurement even by not skilled or specialized personnel.

This object is accomplished, according to the invention, by a procedure characterized in that it comprises the following operations:

exploring, by optical/electrical converter means, the region of the magnified image of the specimen having the impression on it, in order to generate image electrical signals carrying informations indicative of the luminance of the explored region;

drawing from said image signals, by means of an image processing technique, position data indicative of the position of a group of image points taken, on the base of predetermined selection criteria, as belonging to the impression contour, and extrapolating or interpolating, from position data of at least one portion of said points, the position of the characteristic points of said impression.

The invention further proposes, for the purpose stated above, an apparatus for carrying out the above procedure, characterized in that it comprises optical/electrical converter means, able to explore the magnified image region of the specimen with the impression thereon and to generate image electrical signals carrying information indicative of the luminance of the explored region, means for the automatic processing of the image, linked to said optical/electrical converter means and capable of drawing out, from said image signals, position data indicative of the position of a group of image points taken, on the base of predetermined selection criteria, as belonging to the impression contour, and processing means being predisposed to extrapolate or interpolate, from the position data of at least some of the above mentioned points, the position of the characteristic points of said impression.

DETAILED DESCRIPTION

Figure 1:
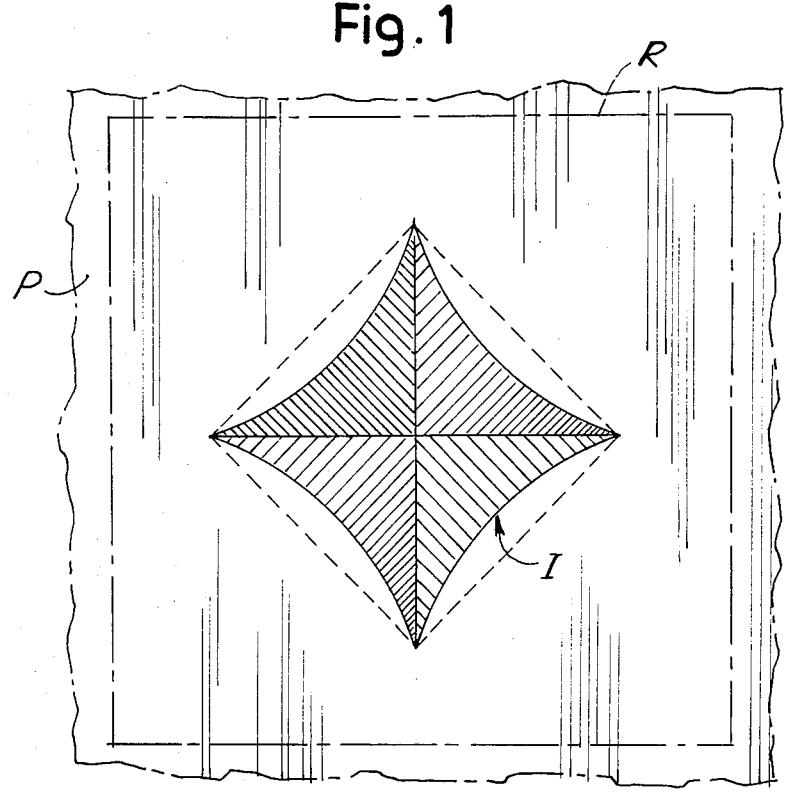
Figure 2:
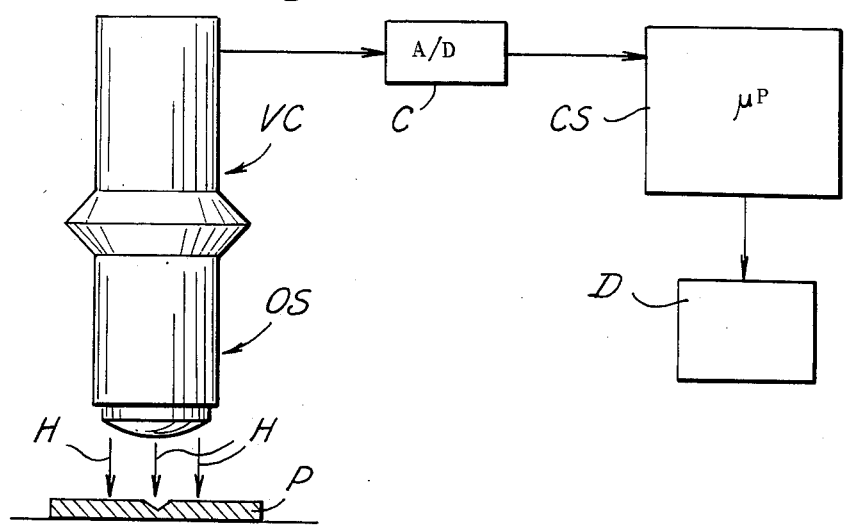
Figure 3:
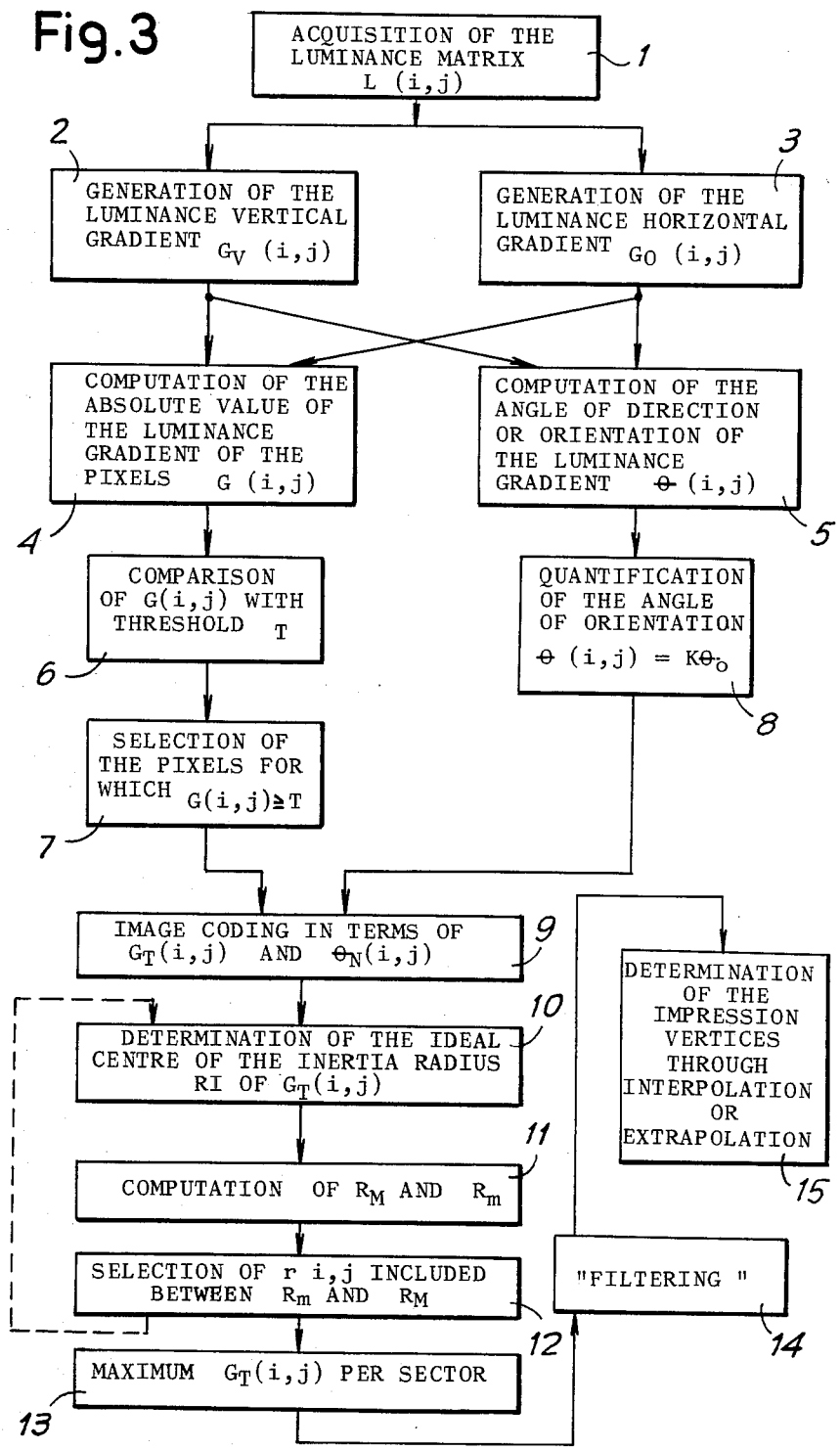
Figure 4:
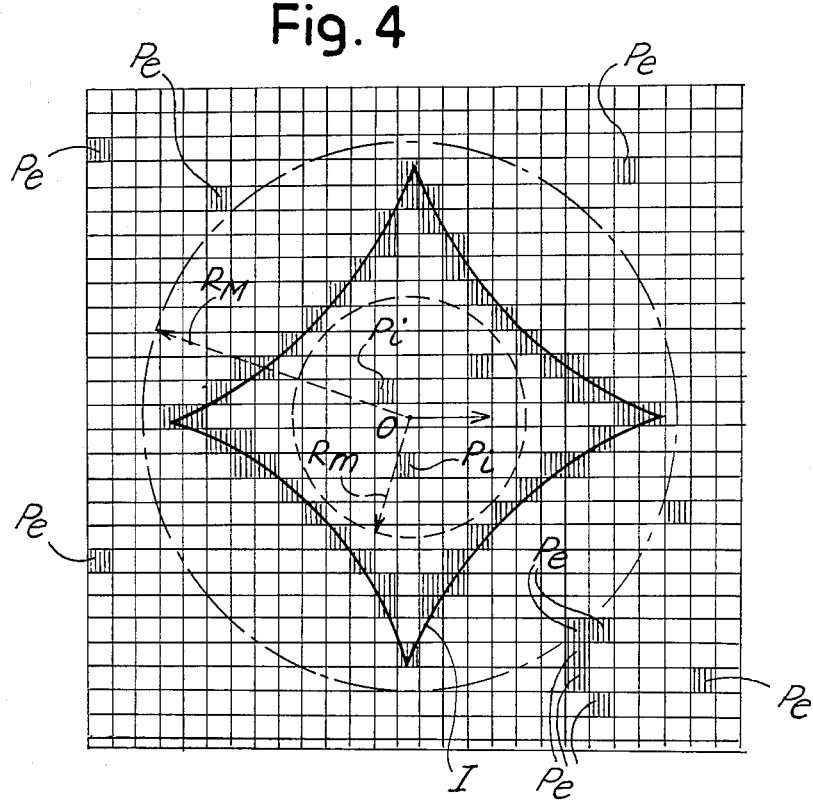
Figure 5:
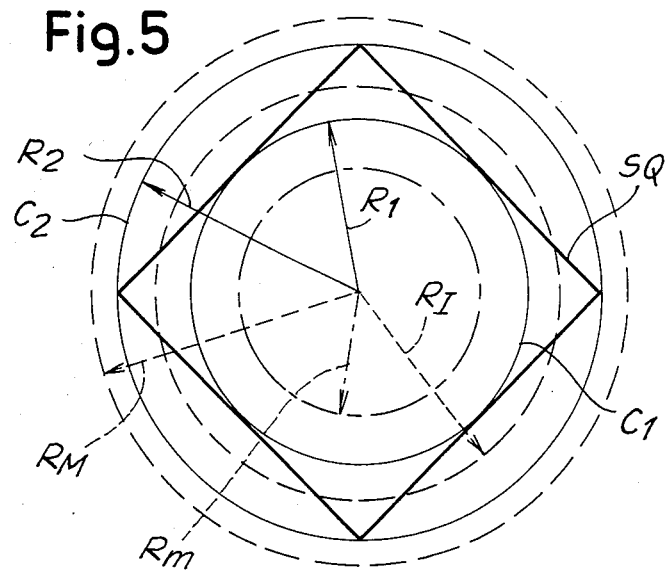

Further characteristics and advantages of the procedure and the apparatus according to the invention will be apparent from the following detailed description which refers, by way of non limitative example only, to the case of the Vickers impression survey performed as shown in the accompanying drawings in which:

FIG. 1 is a plan view, in a very much enlarged scale, of a portion of a specimen having a Vickers impression thereon, FIG. 2 shows an apparatus according to the invention, FIG. 3 is a flow diagram showing the procedure carried out through the apparatus shown in FIG. 2, FIG. 4 is a diagrammatic representation of the luminance gradient of the impression image shown in FIG. 1, and FIG. 5 shows an array of geometrical figures exemplifying some operations performed with the procedure according to the diagram of FIG. 3.

In FIGS. 1 and 2, P indicates a specimen into which, in a well known way, an impression (Vickers impression), designated by I, has been impressed by means of a pyramidal indentor. As illustrated in FIG. 1, the contour of the impression I has a "pseudo-square" shape, with curvilinear sides. In FIG. 1, in order to point out such impression feature, the curvature of these sides has been made more marked than its real feature.

The face of the specimen carrying the impression I is illuminated by the light being collimated through an optical system OS, as shown by way of example by the arrows H of FIG. 2, so that the impression I may appear as a dark, low luminance area on a brighter background having a relatively higher luminance, substantially as it is shown in FIG. 1. The specimen region (indicated by R in FIG. 1) surrounding the impression I is framed and magnified by the optical system OS (FIG. 2) made up, for example, by a microscope with 100–650 magnifications. To the optical system OS a telecamera VC is connected, which provides for the generation of image electrical signals carrying information indicative of the luminance of the region R of the specimen. The image signals generated by the telecamera VC are converted into digital form by an analogue/digital converter C, with its output connected to a computer generally indicated by CS.

As will be apparent by the following, that computer is predisposed for processing the image signals through per se known "image-processing" techniques in order to draw data indicative of the position of a group of points of the analyzed image taken, on the base of predetermined selection criteria, as belonging to the sides of the impression contour I. The computer CS is also predisposed for extrapolating the position of the vertices of the impression I, on the base of the position data of at least a portion of the abovementioned points. A display D is connected to the computer CS in order to give a visible indication of the processing results.

With reference to FIG. 3 a procedure for processing the image R will be now described apt to determine the position of the vertices of the impression I.

Through the telecamera VC and the converter C the information of the image luminance in the region R is transformed into an L(i,j) matrix, each Lij element of which indicates the luminance value of a corresponding point of the image, having coordinates (i,j). The image of the region R is then acquired and stored into computer CS under form of a luminance array or matrix L(i,j) as indicated by the block 1 of FIG. 3.

The computer CS is predisposed to detect, in a way described below, the impression contour I by a technique of enhancement and of comparison with the luminance threshold of the explored image (enhancement thresholding edge detection). Such a technique, well known in the field of image digital processing, is described in detail, for example, in the article of I. E. Abdou and W. K. Pratt, "Quantitative Design and Evaluation of Enhancement/Thresholding Edge Detectors", in the Proceedings of the IEEE, Vol. 67, No. 5, May 1979, pages 753–763.

According to this technique, the above defined luminance matrix L is processed by a differential operator of discrete type, in order to "enhance" the image points corresponding to the impression contour I. According to the preferred embodiment of the invention, vertical and horizontal Sobel differential operators are used owing to their characteristics of isotropy and good sensitivity to the position of the image contour. The horizontal and vertical ($S_o$ and $S_v$) Sobel operators may be defined in matrix form as follows:

$$S_0 = \begin{bmatrix} 1 & 0 & -1 \\ 2 & 0 & -2 \\ 1 & 0 & -1 \end{bmatrix} \quad S_v = \begin{bmatrix} -1 & -2 & -1 \\ 0 & 0 & 0 \\ 1 & 2 & 1 \end{bmatrix}$$

By means of the bidimensional space convolution of the luminance matrix L with the $S_o$ and $S_v$ operators, the matrixes $G_O(i,j)$ and $G_V(i,j)$, are obtained of the horizontal and vertical components of the luminance gradient of the explored image:

$$G_V(i,j) = [L(i-1,j-1) + 2 \cdot L(i-1,j) + L(i-1,j+1)] - [L(i+1,j-1) + 2 \cdot L(i+1,j) + L(i+1,j+1)]$$

$$G_O(i,j) = -[L(i-1,j-1) + 2 \cdot L(i,j-1) + L(i+1,j-1)] + [L(i-1,j+1) + 2 \cdot L(i,j+1) + L(i+1,j+1)]$$

The operations for generating the luminance vertical and horizontal gradient are indicated by the blocks 2 and 3 of the diagram of FIG. 3.

On the base of $G_O$ and $G_V$, the absolute value G and the orientation $\Theta$ of the luminance gradient of each pixel (blocks 4 and 5 of the diagram in FIG. 3) are then calculated:

$$G(i,j) = \sqrt{G_O^2(i,j) + G_V^2(i,j)}$$

$$\theta(i,j) = \arctan\left[\frac{G_V(i,j)}{G_O(i,j)}\right]$$

The absolute value of the luminance gradient of each pixel is then compared with a threshold value T (block 6), and pixels are selected having gradient greater in modulus than the T value (block 7).

The angle of direction or orientation of the luminance gradient in each pixel $\Theta(i,j)$ is preferably "quantized" in k discrete values (block 8).

At this point of the processing, the region R image including the impression I results "coded" through a $G_T$ gradient matrix defined as follows:

$$G_T(i,j) = \begin{cases} G(i,j) & \text{if } G(i,j) \geq T \\ 0 & \text{if } G(i,j) < T \end{cases}$$

and through the matrix $\Theta$ of quantized orientation of the gradient (block 9 in the diagram of FIG. 3).

FIG. 4 shows an exemplifying image of 27×27 pixels, which diagrammatically represents matrix $G_T$: a nul value of the luminance gradient is corresponding to each white pixel (small square) of this image; a non nul value and greater than the threshold T is corresponding to the other pixels.

In FIG. 4 the Vickers impression contour is indicated by I, similarly to FIG. 1.

In general, the gradient $G_T$ results non nul at points located in correspondence of the impression contour I, and also at points external and internal to such contour, like those indicated with $p_e$ and $p_i$, respectively, in FIG. 4. The points $p_e$ and $p_i$ originate from perturbations or irregularities of the luminance (spots) of the analyzed image. Such points constitute a disturbance and, during the successive processing, may cause an incorrect determination of the image contour.

In order to eliminate or at least reduce the influence of such points of disturbance, according to the invention, advantage is taken of the knowledge "a prior" at disposal about the contour shape of the figure to be investigated. In the case under consideration, the impression contour I has a pseudo-square shape.

Let us suppose now that the impression contour I has a perfectly squared shape like, for example, the square indicated by SQ in FIG. 5. The contour of such a square is included between the inscribed circle C1 having radius R1 and the circumscribed circle C2 having radius R2. The radii R1 and R2 depend on the inertia radius RI of the square SQ, as everybody knows, according to the following relations:

$$R1 = \sqrt{3}/2 \cdot RI$$

$$R2 = \sqrt{3}/\sqrt{2} \cdot RI$$

Keeping in mind the above remarks, in order to eliminate the influence of the above points $p_e$ and $p_i$, according to the invention, the following procedure is carried out.

First the position is calculated of the centroid or centre of gravity of the system of points formed by the pixels to which a non nul value of $G_T$ corresponds, that is, the non white pixels of FIG. 4. Such a centroid results on the whole coincident to or little shifted from the geometrical centre of the figure formed by the impression contour I, and in FIG. 4 it has been indicated by O. After introducing a polar reference r, $\theta$ having origin in said centroid, the inertia radius RI of the system of points made up by the pixels to which a non nul value of $G_T$ corresponds (block 10 of the diagram in FIG. 3), is then calculated.

A minimum radius $R_m$ and a maximum radius $R_M$ are then calculated according to the following equations:

$$R_m = \sqrt{3}/2 \cdot RI - 0.2 \cdot RI \simeq 0.67 \cdot RI$$

$$R_m = \sqrt{3}/\sqrt{2} \cdot RI + 0.2 \cdot RI \simeq 1.42 \cdot RI$$

The radii $R_m$ and $R_M$ correspond, substantially, to the radii R1 and R2 of FIG. 5 with, respectively, a decrease and an increase of 20% of the inertia radius RI to take account of the fact that the contour I is never perfectly squared.

This operation is indicated by the block 11 in the flow diagram of FIG. 3.

In the array $G_T(i,j)$ all those terms to which a radial distance from the centroid (O) lower than $R_m$ or greater than $R_M$ corresponds, are then cancelled. In this way, the points $p_e$ and $p_i$ of the luminance gradient $G_T$ of FIG. 4 are eliminated.

For a better arrangement of the results, the operations indicated by blocks 10 and 12 of FIG. 3 may, possibly, be iterated for a number of times.

In the polar reference r, $\theta$ with origin in the centroid O, the variation range $(0,2\pi)$ of the angular coordinate $\theta$ is then divided into a number N of angular sectors having equal amplitude. In each of said angular sectors the computer provides for selecting the pixel to which the maximum value of $G_T$ (block 13 of FIG. 3) corresponds. This pixel is assumed as a potential point ("candidate") of the impression contour I in such angular sector. The set of N points "candidate" to be considered contour points, makes up, in this way, an ordered sequence based on the number n (from 1 to N) which characterizes the angular section it belongs to. Owing to noise effects or possible disturbances (spots, rulings, etc.), some of these "candidate" points may be actually wrong points, that is, not belonging to the contour. To eliminate such points a "filtering" operation (block 14) is then performed. This "filtering" consists in comparing each point of the sequence with a set of points which, in the sequence, make up a neighborhood of it. If the difference between the value of the radial coordinate of the "candidate" point under examination and the average of the radial coordinate values of the points of such neighborhood is below a predetermined value, then, the "candidate" point under examination is definitely assumed as a point of the contour, otherwise, it is replaced by a value obtained from interpolation of the points making up the neighborhood.

The contour of the impression I is thus detected through N points.

The vertices of the impression contour I are then determined by extrapolation or interpolation based on at least some of the N points of the contour detected in the manner described above (block 15 of FIG. 3).

On the base of the coordinates of the vertices of the impression contour I, the computation of the diagonals measurement of same impression and thus of the Vickers hardness of the specimen under test can be performed straightaway.

The flow diagram shown in FIG. 3 may be easily translated in a program for the computer CS.

The results of the processing are visualized through the display D.

The procedure and apparatus according to the invention allow hardness evaluations feasible in a repetitive way, with minimum deviations, thanks to the elimination of any possible subjective evaluation by the operator. In fact, if the optical system is equipped with an automatic focusing device, the whole operation of the apparatus becomes in turn completely automatic.

The technique of extracting the contour with the use of differential operators permits to release the contour detection from the absolute value of the image luminance, and the localization of the contour in correspondence of the maximum gradients of the luminance, results, at least in a first approximated evaluation, relatively unaffected by little blurrings of the image.

Other differential operators, as for example the Prewitt one, may be utilized as well for achieving the gradient of the image luminance.

As an alternative to the above described technique for the extraction of the image contour, other techniques known per se may be utilized. In particular, for the image "segmentation" into its two main components, that is, the impression and the background, particular techniques defined with the English term "region growing" may be utilized.

The apparatus and the procedure according to the invention permit the survey of the Vickers impression and in particular the determination of its vertices position, in a quick, accurate and, above all, repetitive way, as it has been outlined in the foregoing.

The procedure and equipment described above may be easily modified and adapted for the survey of other types of impression, for example, the Knoop-Petersen-Emerson impression (lozenge-like impression), the Berkowitch impression (triangular impression), the Grodzinski impression (boat-like impression) or, as already stated above, for the measurement of two orthogonal diameters in the Brinell impression.

Obviously, without prejudice to the invention, principle, the accomplishment ways and embodiment forms may be widely changed respect to what has been described and illustrated by way of a non limitative example only, without departing from the scope of the present invention.

We claim:

1. A procedure for the detection of the impression (I) made on a specimen (P) in measuring the hardness at penetration, and in particular for the determination of the position of the characteristic points of said impression, for example, the vertices in the Vickers impression, in which the specimen is illuminated so that it creates, in the vicinity of the impression, a variation of the luminance with respect to a neighbouring zone, and in which the image (R) of the impression is then magnified by an optical system (OS), said procedure further including the following operations:

exploring, by optical/electrical converter means (VC; C) the region (R) of the magnified image of the specimen (P) carrying the impression (I) in order to generate image electrical signals carrying information (L) indicative of the luminance of the explored region (R), drawing from said image signals, by means of a technique of image processing, position data indicative of a group of image points taken, on the basis of predetermined selection criteria, as belonging to the impression contour (I), and extrapolating or interpolating, from the position data of at least some of said image points, the position of the characteristic points of said impression.

2. A procedure according to claim 1, characterized in that said group of image points taken as belonging to the sides of the impression contour is detected by enhancement of the luminance (L) of the explored image (R).

3. A procedure according to claim 2, characterized in that said image signals are processed by a differential operator ($S_O$, $S_V$) in order to generate image differential signals ($G_O$, $G_V$) carrying informations indicative of the luminance gradient (G) of said explored region (R); that said image differential signals are compared with at least a predetermined reference datum (T), and that the points of the explored image (R) in which the luminance gradient (G) is greater in modulus than said reference datum (T), are assumed as possible points belonging to the sides of the image contour (I).

4. A procedure according to claim 3, characterized in that it further comprises the operations of:

computing the position of the centroid (O) of the luminance gradient ($G_T$) of the above mentioned explored region (R), assuming such centroid (O) as an origin point of a polar reference system (r, $\theta$), subdividing the field of the angular coordinate ($\theta$) of such reference system (r, $\theta$) into a predetermined number (N) of equal angular sectors, and selecting in each of such sectors the point to which the maximum absolute value of the luminance gradient ($G_T$) corresponds, and assuming such point as a point of the contour of the impression image (I).

5. A procedure according to claim 4, characterized in that the inertia radius (RI) of the luminance gradient ($G_T$) of the points of the explored image, is computed with respect to said centroid (O), a maximum value ($R_M$) of radial coordinate (r) in said polar reference system (r, $\theta$) is established as a function of the value of that inertia radius (RI), and in each of said angular sectors, points are selected having a radial coordinate (r) smaller than or equal to said maximum value ($R_M$), and among these points a point is selected to which the maximum absolute value of the luminance gradient ($G_T$) corresponds, such a point being assumed as a point of the contour of the impression image (I).

6. A procedure according to claim 5, characterized in that said maximum value ($R_M$) of the radial coordinate (r) is equal to or greater than the inertia radius (RI).

7. A procedure according to claim 5, characterized in that a minimum value ($R_m$) of the radial coordinate (r) in said reference polar system (r, $\theta$) is established as a function of said inertia radius (RI), and in each of the above mentioned angular sectors, points are selected whose radial coordinates (r) are comprised between said maximum and minimum value ($R_M$ and $R_m$), and among such points, a point is selected to which the maximum absolute value of the luminance gradient ($G_T$) corresponds, such point being assumed as a point of the contour of the impression image.

8. A procedure according to claim 7, characterized in that said minimum value ($R_m$) of the radial coordinate (r) is less than the inertia radius (RI).

9. A procedure according to claim 5, characterized in that the value of the radial coordinate (r) of each point, assumed as belonging to the contour, is compared with a mean value of the radial coordinates of a predetermined number of points located in the neighborhood of a point under examination, and that the point under examination is definitely assumed as a point of the impression contour provided that the difference between its radial coordinate and said mean value is below a predetermined value.

10. A procedure according to claim 9, characterized in that the point under examination is replaced with a fictitious point determined by interpolation of the coordinates of the points of the neighborhood of the point under examination, when the difference between the radial coordinate of the point under examination and said mean value exceeds said predetermined value.

11. A procedure according to claim 3, characterized in that said differential operator is the non-linear Sobel operator.

12. A procedure according to claim 1, characterized in that the above mentioned group of image points assumed as belonging to the impression contour is detected through a so-called "region growing" technique.

13. A procedure according to claim 1, characterized in that the region (R) of the magnified image of the specimen (P) carrying the impression (I) is explored by a telecamera (VC).

14. An apparatus for the survey, and in particular for the determination of the characteristic points of the impression (I) made on a specimen (P) in measuring the hardness at penetration, including means (OS) to illuminate the specimen (P) to create, in correspondence of the impression (I) a luminance variation (R) respect to the neighbouring zone, and an optical system (OS) to magnify the impression image, characterized in that it comprises optical/electrical converter means (VC; C) apt to explore the region (R) of the magnified image of the specimen (P) carrying the impression (I) and to generate image electrical signals carrying information (L) indicative of the luminance of the explored region, means for automatic processing of the image (CS) linked to said optical/electrical converter means (VC; C) and capable of drawing out from said image signals position data indicative of the position of a group of image points which are assumed, on the basis of predetermined selection criteria, as belonging to the impression contour (CI), and processing means (CS) predisposed to extrapolate or interpolate from the position data of at least some of the above mentioned points, the position of the characteristic points of said impression (I).

15. An apparatus according to claim 14, characterized in that said means for the automatic processing of the image and said processing means constitute a computer system (CS).

16. An apparatus according to claim 15, characterized in that said computer system (CS) is predisposed to carry out a method of detection of the contour of the image explored through the technique of enhancement/thresholding of the luminance of the explored image.

17. An apparatus according to claim 16, characterized in that said computer system (CS) is predisposed for:

treating the above mentioned image signals by means of a differential operator ($S_O$, $S_V$) in order to generate image differential signals carrying informations indicative of the luminance gradient ($G_O$; $G_V$) of the above mentioned explored region (R), comparing said image differential signals with at least a predetermined reference datum (T), and taking as possible points belonging to the impression contour (I) those points of the explored image (R) in which the luminance gradient is greater in modulus than said reference datum.

18. An apparatus according to claim 17, characterized in that said computer system (CS) is predisposed for computing the position of the centroid (O) of the luminance gradient ($G_T$) of the above mentioned explored region (R), taking such centroid (O) as an origin point of a polar reference system (r, $\theta$), subdividing the field of the angular coordinate of such datum (r, $\theta$) into a predetermined number (N) of equal angular sectors, and selecting in each of these sectors the point to which the maximum absolute value of the luminance gradient corresponds, and then assuming such point as a point of the contour of the impression image (I).

19. An apparatus according to claim 18, characterized in that said computer system (CS) is predisposed for computing the inertia radius (RI) of the luminance gradient ($G_T$) of the points of the explored image respect to said centroid (O), establishing, as a function of the value of such inertia radius (RI), a maximum value ($R_M$) of radial coordinate (r) in said polar reference system (r, $\theta$), and selecting, in each of the above mentioned angular sectors, the points having a radial coordinate (r) less than or equal to said maximum value ($R_M$), and then selecting among such points the point to which the maximum absolute value of the luminance gradient ($G_T$) corresponds, such point being assumed as a possible point of the contour of the impression image (I).

20. An apparatus according to claim 19, characterized in that said computer system (CS) is predisposed to establish a maximum value ($R_M$) of the radial coordinate (r) equal to or greater than the above mentioned inertia radius (RI).

21. An apparatus according to claim 19, characterized in that said computer system (CS) is predisposed to establish, as a function of said inertia radius (RI), a minimum value ($R_m$) of the radial coordinate (r) in said polar reference system (r, $\theta$), and to select, in each of said angular sectors, those points whose radial coordinates (r) are included between said maximum and minimum values ($R_M$, $R_m$), and to select among said points, the point to which the maximum absolute value of the luminance gradient ($G_T$), corresponds, such point being assumed as a possible point of the contour of the impression image (I).

22. An apparatus according to claim 21, characterized in that said computer system (CS) is predisposed for selecting a minimum value ($R_m$) of the radial coordinate (r) which is less than the inertia radius (RI).

23. An apparatus according to claim 19, characterized in that said computer system (CS) is predisposed for comparing the value of the radial coordinate (r) of each point taken as possible point of the impression contour, with the mean value of the radial coordinates of a predetermined number of points located in the neighborhood of the point under examination, and for definitely assuming the point under examination as a point of the impression contour (I) provided that the difference between its radial coordinate (r) and said mean value is less than a predetermined value.

24. An apparatus according to claim 23, characterized in that said computer system (CS) is predisposed for replacing the point under examination with a fictitious point determined through interpolation of the coordinates of the points in the neighborhood of the point under examination, when the difference between the radial coordinate (r) of the point under examination and said mean value exceeds said predetermined value.

25. An apparatus according to claim 17, characterized in that said differential operator is the non-linear Sobel operator.

26. An apparatus according to claim 14, characterized in that the above mentioned computer system (CS) is predisposed to detect the above mentioned group of image points taken as belonging to the impression contour (I) by means of the so-called "region growing" technique.

27. An apparatus according to claim 26, characterized in that said optical/electrical converter means include a telecamera (VC).

* * * * *